United States Patent [19]

Sullivan et al.

[11] Patent Number: 4,556,733

[45] Date of Patent: Dec. 3, 1985

[54] PROCESS FOR THE PREPARATION OF 2-HYDROXYBENZENESULFONAMIDE

[75] Inventors: Thomas A. Sullivan; Vincent G. Witterholt, both of Wilmington, Del.

[73] Assignee: E. I. Du Pont de Nemours and Company, Wilmington, Del.

[21] Appl. No.: 619,275

[22] Filed: Jun. 11, 1984

[51] Int. Cl.$^4$ .......................................... C07C 143/78
[52] U.S. Cl. ....................................................... 564/89
[58] Field of Search ........................................ 564/89

[56] References Cited

U.S. PATENT DOCUMENTS 3,127,446  3/1964  Holmes .............................. 564/89 X
3,546,234  12/1970  Fauland et al. ................... 564/89 X
3,803,062  4/1974  Rodia et al. ....................... 564/89 X
3,890,383  6/1975  Rodia et al. ........................... 564/89

OTHER PUBLICATIONS

*Phosphorous and Sulphur*, 1979, vol. 6, pp. 413–419.
*Catalytic Hydrogenation in Organic Synthesis*, Chap. 12.
*J. Chem. Soc.*, 2903 (1958).
JACS 82, 1135 (1960).

*Primary Examiner*—Paul F. Shaver

[57] ABSTRACT

A three step process for preparing 2-hydroxybenzenesulfonamide from 2,4-dichlorophenol by treatment with chlorosulfonic acid followed by amination to form the dichlorohydroxysulfonamide and finally dehalogenation.

15 Claims, No Drawings

PROCESS FOR THE PREPARATION OF 2-HYDROXYBENZENESULFONAMIDE

BACKGROUND OF THE INVENTION

The process of this invention relates to the preparation of 2-hydroxybenzenesulfonamide by a three step process beginning with 2,4-dichlorophenol. More specifically the process of this invention relates to treating 2,4-dichlorophenol with chlorosulfonic acid followed by treatment with ammonia and finally dehalogenation to form 2-hydroxybenzenesulfonamide.

The sulfonamides described in European patent application No. 44,212 (1/20/82) are herbicides showing very high activity. Such compounds have been difficult to prepare. The ready availability of 2-hydroxybenzenesulfonamide (A), would simplify the preparation of these compounds but present routes to (A) involve several steps which proceed in low yields. All known methods to (A) have started with 2-nitrophenol and involve a 6-step sequence similar to that described in *J. Chem. Soc.*, 2903 (1958) and shown in Equation 1.

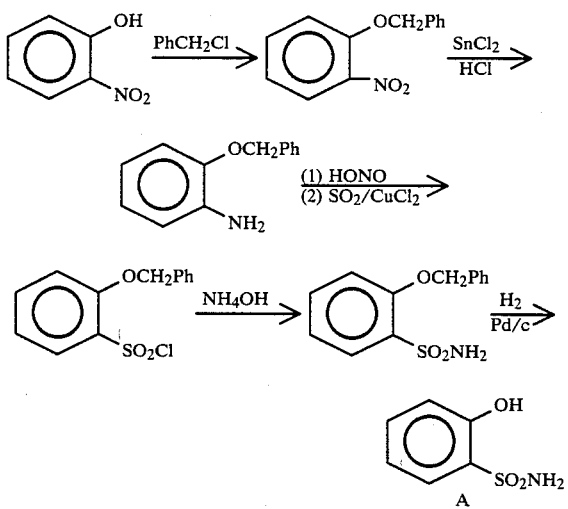

The overall yield for this route was improved to 14% as described in *Chem. Ind.* (London) 888 (1972). Alternately, sulfonates have been used as protecting groups in place of the benzyl group.

Published European patent application No. 44 807 (1/27/82) describes the preparation of (A) via the procedure outlined in Equation 2.

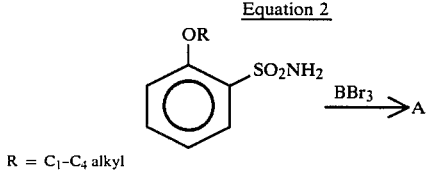

R = C$_1$-C$_4$ alkyl

The starting 2-alkoxybenzenesulfonamides were apparently prepared via a diazotization and coupling sequence similar to that described in Equation 1.

One might approach the synthesis of (A) beginning with phenol, introducing the ortho sulfonamide group via a sulfonation step. Several attempts at this using a variety of conditions and sulfonating reagents all provided a mixture of the ortho and para isomers, which are difficult to separate. The para isomer nearly always predominates (H. Gerfontain, "Mechanistic Aspects in Aromatic Sulfonation and Desulfonation," 1968, pp. 96–102). Thus, one skilled in the art would not pursue this avenue to (A).

A synthetic route is described in *J. Amer. Chem. Soc.*, 82, 1135–1138 (1960) wherein 2-amino-4,6-dichlorobenzenesulfonamide is dehalogenated to 2-aminobenzenesulfonamide (B). If one were to attempt to incorporate a similar step into a route to (A), the preparation of 2-hydroxy-4,6-dichlorobenzenesulfonamide would be necessary. The chlorosulfonation of 3,5-dichlorophenol, however, occurs in the position para to the oxygen to give 2,6-dichloro-4-hydroxybenzenesulfonyl chloride, as described by Cremple and Crongi, *Phosphorus and Sulfur*, 6, 413 (1979). Thus, a scheme paralleling that described for (B) would provide 4-hydroxybenzenesulfonamide rather than (A).

The chlorosulfonation of 2,4-dichlorophenol is also described in the above reference, as is its subsequent amination to prepare 2-hydroxy-3 5-dichlorobenzenesulfonamide. Dehalogenation of aromatic halides is generally known in the art, as described for 2-amino-4,6-dichlorobenzenesulfonamide above; however, dehalogenation of halo-2-hydroxybenzenesulfonamides to provide (A) has not been previously reported.

The current routes to (A) involve the six step, low yield, volume inefficient process involving diazotization chemistry and/or expensive reagents such as boron tribromide (BBr$_3$). Due to the variety of sulfonamides available using (A) as an intermediate, any improvement in its preparation is desirable. In particular, a route in which (A) was provided in a form readily convertible to derivatives such as 2-alkanesulfonyloxy-, 2-alkyloxy-, 2-alkenyloxy-, 2-alkynyloxy-, or 2-acyloxy-benzenesulfonamides would be especially useful.

SUMMARY OF THE INVENTION

Now a process has been found for preparing 2-hydroxybenzenesulfonamide from 2,4-dichlorophenol, said process comprising (1) contacting 2,4-dichlorophenol with at least four equivalents of chlorosulfonic acid, quenching the reaction product in water at 0°–60° C. to form 2-hydroxy-3,5-dichlorobenzenesulfonyl chloride, and optionally adding a chlorocarbon solvent, (2) contacting the sulfonyl chloride from (1) with at least three equivalents of aqueous ammonia or anhydrous ammonia at −5° to 25° C. to form 2-hydroxy-3,5-dichlorobenzenesulfonamide and (3) dehalogenating the sulfonamide by contacting the reaction product from (2) with hydrogen in the presence of at least three equivalents of an alkali metal hydroxide, alkaline earth metal hydroxide, or alkaline earth metal oxide and a palladium or Raney nickel catalyst at at least atmospheric pressure.

In the process of the invention as described above the contacting with chlorosulfonic acid is followed by an aqueous quenching. The use of chilled water in a subsurface quench is preferred. The sulfonyl chloride that is formed may be isolated by filtration or may be dissolved in an appropriate solvent and used directly in the amination step. Preferably, the sulfonyl chloride is not isolated but is taken up in a solvent which is immiscible in the quench mixture. A preferred solvent is a chlorocarbon. Most preferably the solvent is methylene chloride. Before proceeding to the amination step, insoluble impurities are preferably filtered off. The preferred reaction temperature is 35°–40° C. The preferred amount of chlorosulfonic acid is 4.5–7 equivalents and more preferably 4.6–5.4.

In Step 2 of the process of the invention the sulfonyl chloride is contacted either with aqueous or anhydrous ammonia to form 2-hydroxy-3,5-dichlorobenzenesulfonamide. Preferably the concentration of the aqueous ammonia is 28–47% by weight. Most preferably the concentration of aqueous ammonia is 40–47% by weight. The preferred source is aqueous ammonia. Appropriate solvents include halocarbons, secondary alcohols, ether, tetrahydrofuran and dioxane. Preferred solvents include chlorocarbons and most preferred is methylene chloride.

Generally at least three equivalents of ammonia are used in Step 2 but 6–10 equivalents are preferred.

Step 3 of the process of the invention involving dehalogenation is conducted in an aqueous or non-aqueous solvent. Generally this solvent includes water or $C_1$–$C_6$ alcohols. Preferably the solvent is water. Step 3 is conducted in the presence of a base which generally includes alkali metal hydroxides, alkaline earth metal hydroxides, or alkaline earth metal oxides. Preferably the base is sodium hydroxide. Generally the quantity of base is at least three equivalents. The pressure is at least atmospheric. Preferably the pressure is 50–2000 psi. The pressure referred to is of hydrogen. Generally the catalyst is palladium or Raney nickel but preferably it is palladium.

DETAILED DESCRIPTION OF THE INVENTION

The present invention describes a method of transforming 2,4-dichlorophenol into 2-hydroxybenzenesulfonamide, an intermediate important in the production of several sulfonylurea herbicides. The process consists of three steps, each of which can be carried out under a variety of conditions to optimize the process. Step 1 involves transforming a dichlorophenol to a dichlorophenol substituted in the six position with a sulfonyl chloride group. This is aminated in Step 2. Step 3 cleaves the chlorine atoms from the dichlorohydroxybenzenesulfonamide to provide the desired product.

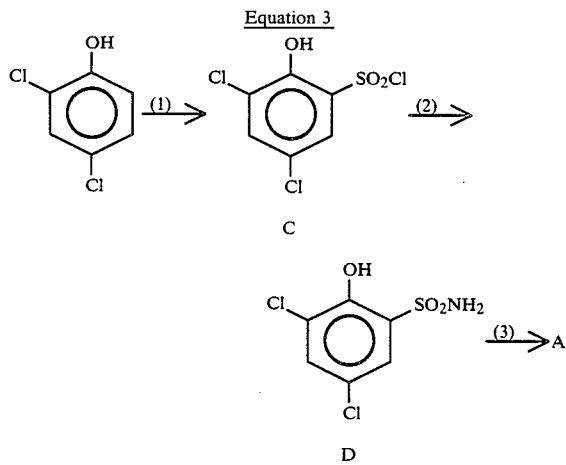

Step 1—Chlorosulfonation

In the first step of the process 2,4-dichlorophenol is contacted with at least 4 (preferably 5) equivalents of chlorosulfonic acid. The phenol may be added as a melt or as a solution in a chlorocarbon solvent. A chlorocarbon solvent may be present with the chlorosulfonic but the preferred method is a neat reaction. A range of temperatures and times will suffice, but the preferred conditions are an addition time of 1–2 hours while maintaining the reaction temperature at 35°–40° C., followed by a 10–30 minute hold at 35°–40° and an additional 30–60 minute hold at 20°–25° C. Faster addition and higher temperatures cause the evolution of HCl to be unmanageable.

More preferred is a reaction identical to the above wherein 2 equivalents of $SOCl_2$ is added to the reaction either before or shortly after the addition of the halogenated phenol. Thus, yields of up to 94% of the sulfonyl chloride can be obtained. Furthermore, only 3 equivalents of chlorosulfonic acid are necessary. This represents an improvement over the art.

While quenching the reaction can be done by carefully contacting the reaction mixture with ice, as taught in the art, the present process involves quenching by slowly pumping the reaction mixture into water. Due to cost and material handling considerations, water is preferred and represents an improvement over ice. The preferred method of quenching involves pumping the reaction mass into a volume of water at least equal to that of the reaction mass while keeping the quench at the desired temperature with cooling. The desired temperature depends on the sulfonyl chloride and the cooling capacity of the equipment (which dictates the length of time over which the quench is carried out). Temperatures of up to 60° C. are satisfactory, but slightly better yields are obtained in the range of 10°–50° C.

Isolation of the product can be accomplished by filtration or by addition of a suitable immiscible solvent to the acidic product slurry. Due to the desirability of transferring a solution to minimize worker exposure, the preferred method involves charging sufficient solvent, most preferably methylene chloride, to dissolve the product, followed by phase separation. This allows the removal of a byproduct not dealt with in the art, namely, 2,4,8,10-tetrachlorodibenzo[1,5,2,6]dioxadithiocin, 6,6,12,12-tetraoxide(E) by in-line filtration.

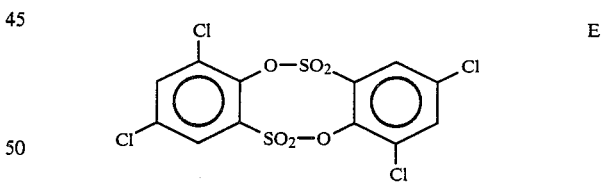

Step 2—Amination

Amination of the sulfonyl chloride obtained in Step 1 can be performed under the following conditions:

(1) The sulfonyl chloride is dissolved in a solvent, such as an alcohol, hydrocarbon, chlorocarbon, or ether. Methylene chloride solutions isolated directly from Step 1 are preferred. This is charged to at least 3 equivalents of 20–47% ammonium hydroxide solution such that the temperature is maintained between −5° and 25° C. The preferred method uses a 30–45% solution of 3,5-dichloro-2-hydroxybenzenesulfonyl chloride in methylene chloride charged to 6–10 equivalents of ammonia as a 40–47% aqueous solution at 0° C. with warming to 10°–15° C. as the reaction proceeds. A larger excess of ammonia gives only slightly improved yield while decreasing the volume efficiency of the reaction. The high concentration of ammonia also increases volume efficiency and provides yields significantly higher than heretofore known (*Phosphorus and Sulfur*, 1979, Vol. 6, pp 413–419). Isolation of the product involves acidification of the reaction mixture to a pH less than or equal to 4.5 followed by filtration. Optionally one can distill the organic solvent off before or after neutralization.

(2) A solution of up to 20% of the 3,5-dichloro-2-hydroxybenzenesulfonyl chloride is cooled to less than 10° C. At least 3 equivalents of anhydrous ammonia are charged into the vessel such that the temperature is maintained below 15° C. The ammonia may be contained within the reactor by means of a cold finger or by using a pressure vessel. Cooling capacity is of utmost importance. If the addition of ammonia takes too long due to poor cooling, an undesired by-product, E, is the major product. The period of addition depends on temperature but should be no longer than 10 hours at 0° C. or 3 hours at 10° C. Once all the ammonia has been added a hold period of at least 30 minutes at 10°–25° C. is necessary to complete the reaction. The product is isolated by acidification and filtration.

Step 3—Dehalogenation

The sulfonamide obtained in Step 2 can be dehalogenated under aqueous or non-aqueous conditions. Preferred is aqueous.

(1) The sulfonamide is dissolved in water with a minimum of 2 equivalents of base. Alkaline metal hydroxides, alkaline earth metal oxides or hydroxides may be used; sodium hydroxide is preferred. The concentration is not critical but it is desirable to have a solution or slurry suitable for pumping. After addition of either optionally supported palladium or Raney nickel, hydrogen is introduced and the reaction is heated. Catalyst loading, pressure and temperature are not critical but should be sufficient to complete the reaction in a reasonable time. Preferred conditions are 5% Pd/C (1 to 5% by weight of the sulfonamide), 3.1 to 5 equivalents of sodium hydroxide as a 10–30% solution, 75°–100° C. and atmospheric pressure up to 2000 psi hydrogen pressure. Completion of the reaction is determined by sampling or by cessation of hydrogen uptake.

The product can be isolated by acidification followed by filtration or extractions with ethyl acetate or other suitable solvents. Optionally, one can use the reaction mixture directly to produce 2-alkylsulfonyloxybenzenesulfonamides which are useful intermediates in the production of herbicides disclosed in European patent application No. 44 212 (1/20/82).

(2) The sulfonamide is dissolved in an alcohol such as n-butyl alcohol. A base, preferably MgO, and catalyst, preferably Pd/C, are added and the reaction is heated to 150°–250° C. under a hydrogen atmosphere of 100–2000 psi until completion.

EXAMPLES

Examples 2, 5, and 6 illustrate the preferred embodiment of this invention.

EXAMPLE 1

Molten 2,4-dichlorophenol (82.13 g) was added to 166 ml of $ClSO_3H$ at 37°–40° C. over a 1 hour period. After a 20 minute hold period at 37°–40° C. the mixture was cooled to 24° C. and held an additional 1 hour. The reaction mixture was then cautiously poured onto 1100 g of ice with constant agitation. Filtration, washing and drying afforded 104 g of 97.6% pure 2-hydroxy-3,5-dichlorobenzenesulfonyl chloride (C) (77% yield), mp 79°–82° C.

EXAMPLE 2

Molten 2,4-dichlorophenol (164.27 g) was added to 332 ml of chlorosulfonic acid at 36°–40° C. over one and one-half hours. After a 10 minute hold period at 38°–40° C. the reaction mixture was cooled to 24° C. and held for 1 hour. This solution was then pumped into 500 ml of water which had been cooled to 5° C. External cooling was required to maintain the quench slurry at 60° C. Once the quench was complete, the slurry was cooled to 45° C. and the agitation was stopped to allow the solids to settle. Using a dipstick, 380 ml of supernatent was removed. This volume was replaced with 180 ml $H_2O$ and 200 ml $CH_2Cl_2$. The organic layer was separated and a second 50 ml wash with $CH_2Cl_2$ was obtained and combined with the first to provide 340 ml, 489 g of a 40.3% solution of (C) in $CH_2Cl_2$ (81% yield).

EXAMPLE 3

Molten 2,4-dichlorophenol (82.7 g) was contacted with 166 ml of chlorosulfonic acid at 37°–40° C. over a 1 hour period. After a 15 minute hold at 40° C. the reaction was cooled to 25° C. and 73 ml of $SOCl_2$ was added. The temperature was raised to 32° C. for 40 minutes and then allowed to cool to 25° C. over 1 hour. The reaction mixture was quenched onto ice. Filtration and drying afforded 126.7 g of 99% pure 2-hydroxy-3,5-dichlorobenzenesulfonyl chloride (C) (94% yield).

EXAMPLE 4

A solution of 39.16 g of the product from Example 3 in 100 ml $CH_2Cl_2$ was contacted with 250 ml of 28% $NH_4OH$ at 5°–8° C. Following removal of $CH_2Cl_2$ by a $N_2$ sparge the mixture was acidified to pH 3. Filtration afforded 42.7 g of 61% pure 2-hydroxy-3,5-dichlorobenzenesulfonamide (D) (71% yield).

EXAMPLE 5

A solution of 53.2 g of the product from Example 4 in 100 ml $CH_2Cl_2$ was contacted with a solution of 21 g $NH_3$ in 25 ml $H_2O$ at $-10°$ to 8° C. Following a 15 mlnute hold time 100 ml $H_2O$ was added and the solution was warmed to 37° C. to remove $CH_2Cl_2$. The solution was then cooled and acidified to pH 1. The precipitate was filtered, washed with water and dried to provide 49.4 g of 88% pure (D) (88% yield).

EXAMPLE 6

A solution of 50 lbs of D, 33 lbs of sodium hydroxide and 183 lbs of water was reduced in the presence of 4 lbs of 5% Pd/C at 75°–90° C. and 400 psig until hydroqen uptake ceased. The solution was filtered to provide 254 lbs of an aqueous solution assayed at 11.1% 2-hydroxybenzenesulfonamide and 0.3% 3-chloro-2-hydroxybenzenesulfonamide, present as their sodium salts.

EXAMPLE 7

An aqueous solution containing 59.2 g of A, obtained as a sodium salt as in Example 6, was cooled to 5° C. Ethanesulfonyl chloride (47 ml, 1.3 equivalents) was added in one portion and the cooling bath was removed. After 45 minutes the product slurry was filtered. The precipitate was washed with water and xylene to provide 46.5 g of 2-ethanesulfonyloxybenzenesulfonamide, mp 90°–92.5° C. (51% yield).

We claim:

1. A process comprising (1) contacting 2,4-dichlorophenol with at least 4 equivalents of chlorosulfonic acid and 0–2 equivalents of thionyl chloride, quenching the reaction product in water at 0°–60° C. to form 2-hydroxy-3,5-dichlorobenzenesulfonyl chloride, and optionally adding a chlorocarbon solvent, (2) contacting the sulfonyl chloride from (1) with at least 3 equivalents of aqueous ammonia or anhydrous ammonia at −5° to 25° C. to form 2-hydroxy-3,5-dichlorobenzenesulfonamide and (3) dehalogenating the sulfonamide by contacting the reaction product from (2) with hydrogen, in a solvent, in the presence of at least two equivalents of a base and a catalyst at a pressure of at least one atmosphere.

2. The process of claim 1 wherein the sulfonyl chloride of Step 1 is dissolved in a chlorocarbon solvent.

3. The process of claim 2 wherein the chlorocarbon is methylenechloride.

4. The process of claim 1 wherein the temperature for Step (1) is 35°–40° C.

5. The process of claim 1 wherein 4.5–7.0 equivalents of chlorosulfonic acid are used.

6. The process of claim 1 wherein 4.6–5.4 equivalents of chlorosulfonic acid are used.

7. The process of of claim 1 wherein 2 equivalents of thionyl chloride are used.

8. The process of claim 1 wherein anhydrous ammonia is used.

9. The process of claim 1 wherein 40–47% aqueous $NH_4OH$ is used.

10. The process of claim 1 wherein 6–10 equivalents of ammonia are used.

11. The process of claim 1 wherein the solvent of Step (3) is $C_1$–$C_6$ alcohol.

12. The process of claim 1 wherein the solvent of Step (3) is water.

13. The process of claim 1 wherein the base of Step (3) is an alkali metal hydroxide, an alkaline earth metal hydroxide or alkaline earth metal oxide.

14. The process of claim 1 wherein the pressure in Step (3) is one atmosphere up to 2000 psi.

15. The process of claim 1 wherein the catalyst is palladium or nickel.

* * * * *